United States Patent
Crafford et al.

[11] 3,971,245
[45] July 27, 1976

[54] WEAR TESTING DEVICE

[75] Inventors: Joseph C. Crafford, Newport News; Vincent J. Dowling, Jr., Yorktown; James A. Gusack, Williamsburg, all of Va.

[73] Assignee: Dow Badische Company, Williamsburg, Va.

[22] Filed: June 18, 1975

[21] Appl. No.: 587,932

[52] U.S. Cl. .................................................. 73/7
[51] Int. Cl.² .......................................... G01N 3/56
[58] Field of Search ............... 73/7, 432 SD, 9, 159

[56] References Cited
UNITED STATES PATENTS

| | | | |
|---|---|---|---|
| 3,134,255 | 5/1964 | Oliver, Jr. et al. | 73/7 |
| 3,516,281 | 6/1970 | Taub | 73/7 |

*Primary Examiner*—Richard C. Queisser
*Assistant Examiner*—John S. Appleman
*Attorney, Agent, or Firm*—George F. Helfrich

[57] ABSTRACT

A cylinder for supporting a fabric sample to be wear tested is mounted for rotation about its longitudinal axis and simultaneous reciprocation along its longitudinal axis. The sample to be wear tested is secured to the cylinder so that the inner surface of the sample is in congruity with the exterior of the major surface of the cylinder. Provided in proximity to the cylinder are a plurality of plates which are spaced from each other along the length of the cylinder, each plate affixed on one major surface to a separate rod with the free major surface of each plate positioned so that it may contact the outer surface of the sample. Each rod is attached at its other end to a crankshaft, by means of which a reciprocating motion is imparted to each rod, whereby each plate is moved back and forth from a position away from the sample to a position in contact with the sample. Means for allowing simultaneous reciprocation and oscillation of each rod is provided, so that as contact between each plate and the sample is effected, the cylinder is caused to rotate about is longitudinal axis. Means for mounting and driving the crankshaft are also provided, as is means for affording reciprocation of the cylinder along its longitudinal axis.

6 Claims, 1 Drawing Figure

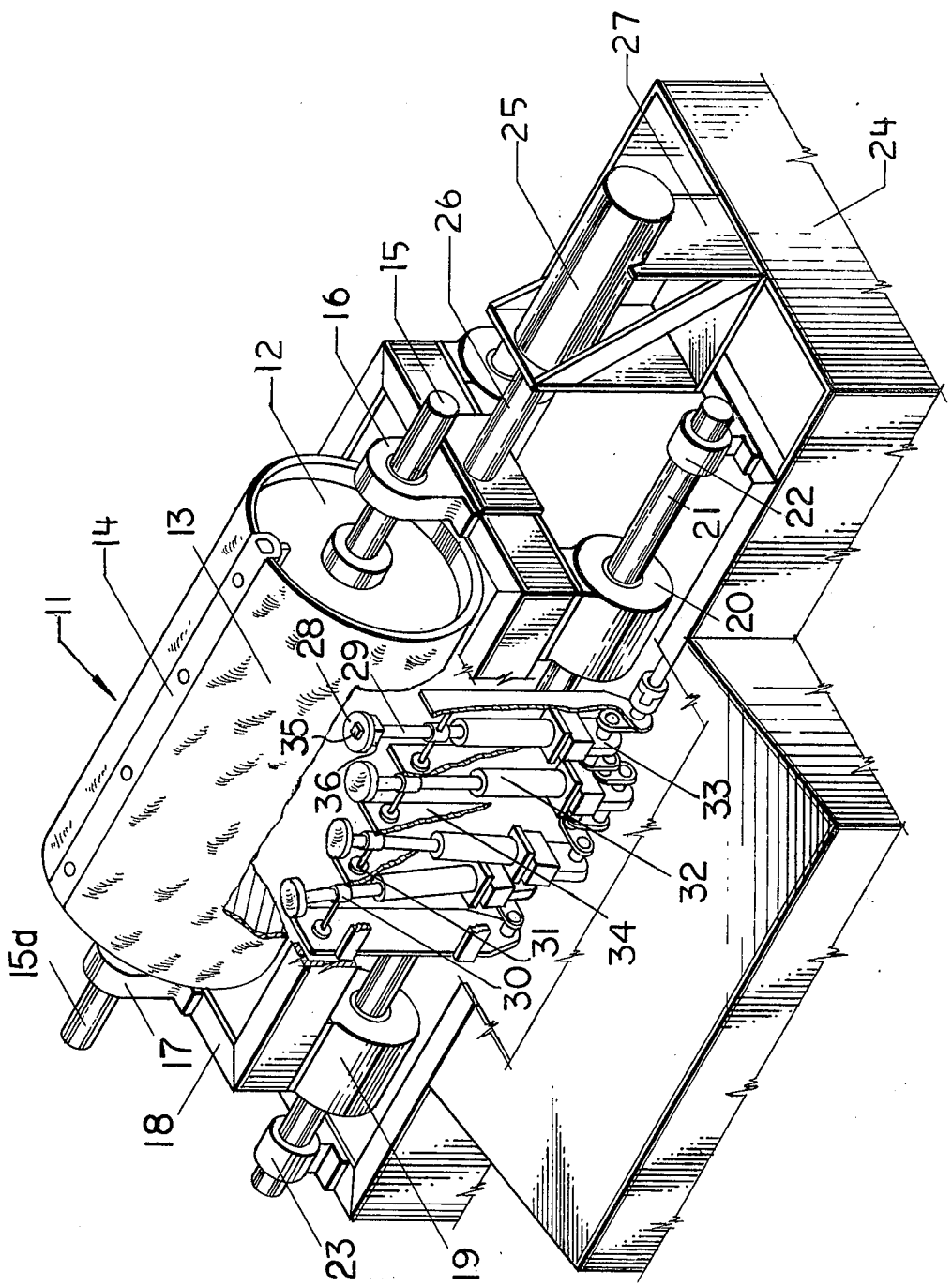

WEAR TESTING DEVICE

BACKGROUND OF THE INVENTION

1. Field of the Invention

This invention relates generally to measuring and testing. It relates in particular to a device for the wear testing of fabrics, especially carpets.

2. Prior Art

Fabrics such as carpets are expected to have good appearance-retention over their useful life. In addition, static-protected constructions are expected to protect against the accumulation of undesirably high charges of static electricity over their useful life. For these and similar reasons, many fabric constructions are routinely subjected to wear under actual service conditions, in order to determine the durability of various properties, thereby affording a prediction of the suitability of the construction in certain proposed applications.

Because of the lengthy periods of time often required for wear testing under actual service conditions (e.g., the time required to achieve 100,000 actual walkons of a sample of carpet — as determined by electronic counting devices — may be as long as 1–3 years), devices achieving accelerated fabric wear have been earnestly sought after by the industry for quite some time.

Consequently, many expedients have been proposed, and a number of devices embodying these expedients have been manufactured and sold. As an example, one such device comprises a metal cylinder having the fabric sample to be tested affixed to the inside surface of the cylinder. Four aluminum bars, each 2 inches square by 6 inches long and coated with a tough polymeric material, are placed inside the cylinder to tumble randomly and produce an abrasive action on the fabric sample as the cylinder is caused to rotate about its longitudinal axis. Notwithstanding the efficacy of this device and similar devices of the prior art (e.g., tests show a reasonably good correlation between in service stroll tests conducted on samples of carpets which were subjected to 85,000 walkons and like samples which were subjected to six hours abrasive action in this device), they are found wanting, — e.g., in that the carpet constructions are not worn in a manner which closely approximates that effected by the shoe of a human. For example, the "beating" abrasive action of many of the prior art devices makes it impossible to accurately assess the changes in shade in a traffic pattern, which would result when a yarn tuft is first flexed in one direction and then in the opposite direction as the foot of a human contacts the carpet sample and then leaves it.

SUMMARY OF THE INVENTION

Accordingly, it is the primary object of the present invention to provide a fabric wear testing device which overcomes the aforementioned inadequacies of prior art devices by closely simulating the wearing effect produced by the shoe of a human walking across the fabric construction.

This object is achieved by providing a device which comprises:

a. a cylinder for supporting the sample to be wear tested, the cylinder having means for securing the inner surface of the sample in congruity with the exterior of the major surface of the cylinder;

b. mounting means for permitting rotation of the cylinder about its longitudinal axis and simultaneous reciprocation of the cylinder along its longitudinal axis;

c. a plate affixed on one major surface thereof to a rod, the free major surface of the plate positioned so that it may contact the outer surface of the sample;

d. a crankshaft, to which the free end of the rod is attached, and by means of which a reciprocating motion is imparted to the rod, so that the plate is moved back and forth from a position away from the sample to a position in contact with the sample;

e. means for allowing simultaneous reciprocation and oscillation of the rod (e.g., a sliding bearing such as a ball bushing coacting with two flange cartridge bearings) so that as contact between the plate and the sample is effected, the cylinder is caused to rotate about its longitudinal axis;

f. means for mounting and driving the crankshaft; and g. means affording reciprocation of the cylinder along its longitudinal axis.

An especially preferred embodiment of the device comprises a plurality of plates spaced from each other along the length of the cylinder, each plate affixed on one major surface thereof to a separate rod, each rod being attached at the other end thereof to the crankshaft.

Moreover, it has been found of particular advantage if an air cylinder is secured between the crankshaft and the means for allowing simultaneous reciprocation and oscillation of each rod, whereby control of the force of each plate contacting the sample is provided.

Furthermore, it is very beneficial in some applications if shoe sole material is affixed to the free major surface of each plate. In this regard, it is also of special advantage if means are provided for monitoring electrostatic charge on the shoe sole material or on the sample.

BRIEF DESCRIPTION OF THE DRAWING

For a more complete understanding of the present invention, reference should be made to the detailed description of the preferred embodiments thereof, which is set forth below. This detailed description should be read together with the accompanying drawing, which is a cutaway perspective schematically illustrating a preferred embodiment according to the present invention.

DETAILED DESCRIPTION OF THE PREFERRED EMBODIMENTS

With particular reference to the drawing, there is shown a device 11, which is a preferred embodiment according to the present invention. Device 11 has a cylinder 12 for supporting sample 13 for wear testing. Cylinder 12, which is advantageously constructed of metal and is closed at both ends, is mounted for rotation about its longitudinal axis by means of mounting shafts 15 and 15a, which are secured to the ends of the cylinder and rotate inside self-aligning ball bearings 16 and 17, respectively, which are fixedly mounted on rectangular frame 18. Cylinder 12 is provided with securing means such as lock fastener 14, which ensures that the inner surface of sample 13 and the exterior of the major surface of cylinder 12 are maintained in congruity.

Sliding bearings such as ball bushings are provided at each of the four corners of rectangular frame 18 on the under side thereof. (Two of these bearings, viz. ball bushings housed in retainers 19 and 20, may be seen in the drawing.) These sliding bearings cooperate with two stationary bars, which are located under frame 18 and positioned parallel to the longitudinal axis of cylinder 12, to allow reciprocation of cylinder 12 along its longitudinal axis. (Seen in the drawing is one such bar 21, which, permanently secured to support structure 24 by securing and aligning means 22 and 23, is slidably attached to rectangular frame 18 by means of the ball bushings housed in retainers 19 and 20.) Actual reciprocation of cylinder 12 along its longitudinal axis is afforded by standard means such as air cylinder 25, which is readily available commercially and is mounted on support structure 24 by means of stationary mount 27. Piston 26 of air cylinder 25 is secured to rectangular frame 18, providing the reciprocating movement of frame 18 in the direction of the longitudinal axis of cylinder 12, in response to programmed changes in the fluid pressure inside air cylinder 25.

Located directly below cylinder 12 is plate 28, which is positioned so that one major surface thereof may firmly contact sample 13. Plate 28 is attached at its other major surface to a rod (advantageously piston 29 of air cylinder 32, as shown in the drawing and hereinafter more completely set forth), which communicates with crankshaft 33. A reciprocating motion is imparted to the rod by means of crankshaft 33, so that plate 28 is moved back and forth from a position away from sample 13 to a position in firm contact therewith. Although the configuration just described is completely acceptable, it has been found of especial advantage to provide a plurality of plates, spaced from each other along the length of cylinder 12, each plate affixed on one major surface thereof to a separate rod which communicates with crankshaft 33. Four such plates are shown in the drawing, each of which is individually attached to a separate rod, which, as shown, is advantageously the piston of an air cylinder secured to crankshaft 33. This configuration is especially preferred, as the air cylinders provide positive control of the force of each plate contacting the sample. For example, it is customary to set the fluid pressure inside each air cylinder to result in the application of 150 pounds of force by each plate to the sample.

Retainer 30 houses a ball bushing, which coacts with an opposed pair of flange cartridge bearings (one of which is shown as 31 mounted on vertical support member 34) to permit the simultaneous reciprocation and oscillation of rod 29, so that as contact between plate 28 and sample 13 is made, the force of such contact will have a component directed tangentially to the surface of cylinder 12. As a result, cylinder 12 is caused to rotate about its longitudinal axis, and a scuffing action is imparted to sample 13, very closely simulating that of a human foot as it contacts a floor covering and then leaves it. Crankshaft 33 is mounted and driven by standard means (not shown) such as an electric motor.

In order to even more closely approximate the wearing effect produced by the shoe of a human contacting a fabric construction, an especially preferred embodiment of the present invention comprises shoe sole material — e.g. leather, rubber, polyvinyl chloride, etc., (not shown) — affixed to the free major surfaces of all plates such as 28. When such is accomplished, it is of considerble advantage to attach an electrode 35 to the shoe sole material on a chosen plate and to connect the electrode to an electrostatic detection head 36. Hereby it is possible to measure and record the static electricity accumulated on the shoe sole material as it contacts and leaves the fabric sample, and the effects of wear on such accumulation may be carefully observed. (Using similar means it is also possible to measure and record the static electricity accumulated on the fabric sample.)

EXAMPLE

A device was constructed essentially as pictured in the drawing. Four disc-like plates such as 28 were employed, each having a diameter of 4⅞ inches and covered with leather shoe sole material. Air cylinders 32 were set to cause each of the plates to exert a force of 150 pounds upon the fabric sample 13. The means (not shown) for driving the air cylinder 25 were adjusted to cause frame 18 to reverse the direction of its travel after reaching the allowed limit of its travel, after each plate had contacted the sample at least once and preferably many times to equalize the wear. A section of standard plush carpeting was placed over cylinder 12 and secured in congruity with the outer surface thereof by means of lock fastener 14. The device 11 was turned on and allowed to operate for 25,000 cycles (100,000 total contacts of plates with the carpet sample). The elapsed time was 14 hours. The carpet sample 13 was then removed and compared with an identical section of the same carpet which had been subjected to 100,000 actual step-ons (as determined by an electronic counting device) in the corridor of an office building, where it had been exposed to normal traffic for about 5 months. The two carpet samples were virtually identical, exhibiting substantially the same degree of appearance retention.

The device of the present invention has been described in detail with respect to certain embodiments thereof. However, it is clear to those of skill in the art that variations and modifications in this detail may be made without any departure from the spirit and scope of the present invention as defined in the hereto-appended claims.

What is claimed is:

1. A device for the wear testing of fabric samples such as carpets, which device comprises:
    a. a cylinder for supporting the sample to be wear tested, the cylinder having means for securing the inner surface of the sample in congruity with the exterior of the major surface of the cylinder;
    b. mounting means for permitting rotation of the cylinder about its longitudinal axis and simultaneous reciprocation of the cylinder along its longitudinal axis;
    c. a plate affixed on one major surface thereof to a rod, the free major surface of the plate positioned so that it may contact the outer surface of the sample;
    d. a crankshaft, to which the free end of the rod is attached, and by means of which a reciprocating motion is imparted to the rod, so that the plate is moved back and forth from a position away from the sample to a position in contact with the sample;
    e. means for allowing simultaneous reciprocation and oscillation of the rod so that as contact between the plate and the sample is effected, the cylinder is caused to rotate about its longitudinal axis;
    f. means for mounting and driving the crankshaft; and g. means affording reciprocation of the cylinder along its longitudinal axis.

2. The device of claim 1, which includes a plurality of plates spaced from each other along the length of the cylinder, each plate affixed on one major surface thereof to a separate rod, each rod being attached at its other end to the crankshaft.

3. The device of claim 2, wherein an air cylinder is secured between the crankshaft and the means for allowing simultaneous reciprocation and oscillation of each rod, whereby control of the force of each plate contacting the sample is provided.

4. The device of claim 2, wherein each plate has shoe sole material affixed to the free major surface thereof.

5. The device of claim 4, which in addition includes means for monitoring electrostatic charge on the shoe sole material.

6. The device of claim 1, wherein the means for allowing simultaneous reciprocation and oscillation of the rod is a sliding bearing.

* * * * *